(12) United States Patent
Miller et al.

(10) Patent No.: US 10,967,077 B2
(45) Date of Patent: *Apr. 6, 2021

(54) IMAGING OF METASTATIC OR RECURRENT CANCER

(71) Applicant: Blue Earth Diagnostics Limited, Oxford (GB)

(72) Inventors: Matthew Miller, Oxford (GB); David Gauden, Oxford (GB); David Schuster, Atlanta, GA (US); Stefano Fanti, Bologna (IT); Cristina Nanni, Bologna (IT); Lucia Zanoni, Bologna (IT); Frode Willoch, Oslo (NO); Trond Velde Bogsrud, Oslo (NO); Tore Bach-Gansmo, Oslo (NO); Alessandra Musto, Bologna (IT)

(73) Assignee: Blue Earth Diagnostics Limited, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/907,863

(22) Filed: Jun. 22, 2020

(65) Prior Publication Data
US 2020/0316228 A1 Oct. 8, 2020

Related U.S. Application Data

(63) Continuation of application No. 16/160,227, filed on Oct. 15, 2018, now Pat. No. 10,716,868, which is a continuation of application No. 14/983,746, filed on Dec. 30, 2015, now Pat. No. 10,124,079.

(51) Int. Cl.
*A61K 51/04* (2006.01)

(52) U.S. Cl.
CPC .............................. *A61K 51/0402* (2013.01)

(58) Field of Classification Search
None
See application file for complete search history.

(56) References Cited

U.S. PATENT DOCUMENTS

| | | |
|---|---|---|
| 8,753,605 B2 | 6/2014 | Cheng et al. |
| 10,124,079 B2 | 11/2018 | Miller et al. |
| 2010/0316636 A1 | 12/2010 | Radin et al. |

FOREIGN PATENT DOCUMENTS

WO WO 1997/017092 A1 5/1997

OTHER PUBLICATIONS

Akhurst, T. et al., "PET-based Whole Body dosimetry of $^{18}$F-FACBC, a Tumor-avid Non-metabolized Amino Acid: Initial Results in Patients," *J. Nucl. Med.* vol. 47, Suppl. 1, p. 492, (2006) (2 pages).

Amzat, R. et al., "Unusual Presentations of Metastatic Prostate Carcinoma as Detected by Anti-1-amino-3-[$^{18}$F]fluorocyclobutane-1-carboxylic acid (anti-3-[$^{18}$F] FACBC) PET-CT," *Clin. Nucl. Med.*, vol. 36, No. 9, pp. 800-802 (2011) (16 pages).

Amzat, R. et al., "Pilot Study of the Utility of the Synthetic PET Amino-Acid Radiotracer Anti-1-Amino-3-[$^{18}$F]. Fluorocyclobutane-1-Carboxylic Acid for the Noninvasive Imaging of Pulmonary Lesions," *Mol. Imaging Biol.* vol. 15, pp. 633-643 (2013).

Asano, Y. et al., "Phase I Clinical Study of NMK36: A New PET Tracer with the Synthetic Amino Acid Analogue Anti-[$^{18}$F]FACBC," *Ann. Nucl. Med.*, vol. 25, pp. 414-418 (2011).

Beheshti, M. et al., "Fluorocholine PET/Computed Tomography Physiologic Uptake, Benign Findings, and Pitfalls," *PET Clin.* vol. 9, pp. 299-306 (2014).

Beyer, T. et al., "Acquisition Protocol Considerations for Combined PET/CT Imaging," *J. Nucl. Med.*, vol. 45, pp. 25S-35S (2004).

Boellaard, R. et al., "FDG PET and PET/CT: EANM Procedure Guidelines for Tumour PET Imaging: Version 1.0," *Eur. J. Nucl. Med. Mol. Imaging*, vol. 37, pp. 181-200 (2010).

Bouchelouche, K. et al., "Positron Emission Tomography and Positron Emission Tomography/Computerized Tomography of Urological Malignancies: An Update Review," *J. Urol.*, vol. 179, pp. 34-45 (2008).

Brown, C. et al., "Investigation of $^{18}$F-FDG 3D Mode PET Image Quality Versus Acquisition Time," *Nucl. Med. Comm.*, vol. 31, pp. 254-259 (2010).

Brunocilla, E. et al., "First Case of 18F-FACBC PET/CT-guided Salvage Radiotherapy for Local Relapse After Radical Prostatectomy with Negative 11C-Choline PET/CT and Multiparametric MRI: New Imaging Techniques May Improve Patient Selection,"*Archivio Italiano di Urologia e Andrologia*, vol. 86, No. 3, pp. 239-240 (2014).

Castellucci, P., et al., "PET/CT in Prostate Cancer: Non-choline Radiopharmaceuticals," *Q.J. Nucl. Med. Mol. Imaging*, vol. 56, No. 4, pp. 367-374 (2012).

Chan, G. et al., "Supraclavicular Lymphadenopathy as the Initial Presentation of Metastatic Prostate Cancer: A Case Report and Review of Literature," *Can. Urol. Assoc. J*, vol. 7, Nos. 5-6, pp. E433-E435 (2013).

Doi, Y. et al., "Evaluation of Trans-1-Amino-3-18F-Fluorocyclobutanecarboxylic Acid Accumulation in Low-Grade Glioma in Chemically Induced Rat Models: PET and Autoradiography Compared with Morphological Images and Histopathological Findings," *Nucl. Med. Biol.*, vol. 42, pp. 664-672 (2015).

European Medicines Agency, "Guideline on Core SmPC and Package Leaflet for Fludeoxyglucose ($^{18}$F). EMA/CHMP/448228/2012," Committee for Medicinal Products for Human Use (CHMP), pp. 1-21 (2012).

Fedorov, A. et al., "3D Slicer as an Image Computing Platform for the Quantitative Imaging Network," *Magn. Reson. Imaging*, vol. 30, No. 9, pp. 1323-1341 (2012) (28 pages).

(Continued)

*Primary Examiner* — Jennifer Lamberski
(74) *Attorney, Agent, or Firm* — Bookoff McAndrews, PLLC

(57) ABSTRACT

The present disclosure relates to methods of administering [$^{18}$F]-FACBC. The present disclosure also relates to use of [$^{18}$F]-FACBC in methods for imaging, diagnosing and monitoring metastasis or recurrence of cancer.

2 Claims, 5 Drawing Sheets

(56) References Cited

OTHER PUBLICATIONS

Giovacchini, G. et al., "[$^{11}$C]Choline Positron Emission Tomography/Computerized Tomography to Restage Prostate Cancer Cases with Biochemical Failure After Radical Prostatectomy and No Disease Evidence on Conventional Imaging." *J. Urology*. vol. 184. pp. 938-943 (2010).

Giovacchini, G. et al., "Do We Have to Withdraw Antiandrogenic Therapy in Prostate Cancer Patients Before PET/CT with [$^{11}$C]Choline?" *Eur. J. Nucl. Med. Mol. Imaging*, vol. 38, pp. 1964-1966 (2011).

Heiss, W. "Clinical Impact of Amino Acid PET in Gliomas," *J. Nucl. Med.*, vol. 55, No. 8, editorial (2014) (3 pages).

Hövels, A. et al., "The Diagnostic Accuracy of CT and MRI in the Staging of Pelvic Lymph Nodes in Patients with Prostate Cancer: A Meta-Analysis," *Clinical Radiology*, vol. 63, No. 4, pp. 387-395 (2008).

Husarik, D.B. et al., "Evaluation of [18F]-Choline PET/CT for Staging and Restaging of Prostate Cancer," *Eur. J. Nucl. Med. Mol. Imaging*, vol. 35, pp. 253-263 (2008).

Inoue, Y. et al., "Phase IIa Clinical Trial of Trans-1-Amino-3-$^{18}$F-Fluoro-Cyclobutane Carboxylic Acid in Metastatic Prostate Cancer," *Asia Oceania J. Nucl. Med. Biol.*, vol. 2, No. 2, pp. 87-94 (2014).

Jager, P. et al., "Radiolabeled Amino Acids: Basic Aspects and Clinical Applications in Oncology," *J. Nucl. Med.*, vol. 42, No. 3, pp. 432-445 (2001).

Jackson, et al., "Prevalence and Patterns of Physiologic Muscle Uptake Detected With Whole Body 18F-FDG PET. 2000", *Journal of Nuclear Medicine Technology*, vol. 34, pp. 29-33 (2006).

Johansson, S. et al., "Initial Imaging Findings Using [$^{18}$F]GE-148 ([$^{18}$F]FACBC) PET/CT in Subjects with Primary Prostate Cancer," *J. Clinical Oncology*, vol. 28, No. 15, Suppl. (2010), abstract (2 pages).

Kairemo, K. et al., "Preliminary Clinical Experience of Trans-1-Amino-3-($^{18}$)F-Fluorocyclobutanecarboxylic Acid (anti-($^{18}$)F-FACBC) PET/CT Imaging in Prostate Cancer Patients," *BioMed Research International*, pp. 1-7 (2014).

Kanagawa, M. et al., "Comparison of Trans-1-Amino-3-[$^{18}$F]Fluorocyclobutanecarboxylic Acid (anti-[$^{18}$F]FACBC) Accumulation in Lymph Node Prostate Cancer Metastasis and Lymphadenitis in Rats," *Nucl. Med. Biol.*, vol. 41, pp. 545-551 (2014).

Klein, S. et al., "Elastix: A Toolbox for Intensity-Based Medical Image Registration," *IEEE Trans Med Imaging*, vol. 29, No. 1, pp. 196-205 (2010).

Komar, G. et al., "Comparison of 2D and 3D Performance for FDG PET with Different Acquisition Times in Oncological Patients," *Nuclear Medicine Communications*, vol. 30, pp. 16-24 (2009).

Laverman, P. et al., "Fluorinated Amino Acids for Tumour Imaging with Positron Emission Tomography," *Eur. J. Nucl. Med.*, vol. 29, pp. 681-690 (2002).

Li, R. et al., "Expression of Neutral Amino Acid Transporter ASCT2 in Human Prostate," *Anticancer Research*, vol. 23, pp. 3-8 (2003).

Marchan, E. et al., "Impact of FACBC PET in Imaging and GTV Design of Cerebral Gliomas," *International J. Radiation Oncology*, 2120, p. S250 (2014).

McConathy, J. et al., "Radiohalogenated Nonnatural Amino Acids as PET and SPECT Tumor Imaging Agents," *Medicinal Research Reviews*, vol. 32, No. 4, pp. 868-905 (2012).

McParland, B. et al., "The Clinical Safety, Biodistribution and Internal Radiation Dosimetry of [$^{18}$F]Fluciclovine in Healthy Adult Volunteers," *Eur. J. Nucl. Med. Mol. Imaging*, ISSN 1619-7070 (2013) (11 pages).

Molina-Duran, F. et al., "Dependence of Image Quality on Acquisition Time for the PET/CT Biograph mCT." *Z. Med. Phys.*, vol. 24, No. 1, pp. 73-79 (2014).

Murphy, R. et al., "The Utility of $^{11}$C-Choline PET/CT for Imaging Prostate Cancer: A Pictorial Guide," *Nucl. Med. Mol. Imaging*, vol. 196, pp. 1390-1398 (2011).

Nanni, C. et al., "Comparison of $^{18}$F-FACBC and $^{11}$C-Choline PET/CT in Patients with Radically Treated Prostate Cancer and Biochemical Relapse: Preliminary Results," *Eur. J. Nucl. Med. Mol. Imaging*, pp. 1-7 (2013).

Nanni, C. et al., "The Detection of Disease Relapse After Radical Treatment for Prostate Cancer: Is Anti-3-$^{18}$F-FACBC PET/CT a Promising Option?" *Nuclear Medicine Communications*, vol. 24, pp. 831-833 (2013).

Nanni, C. et al., "$^{18}$F-FACBC Compared with $^{11}$C-Choline PET/CT in Patients with Biochemical Relapse After Radical Prostatectomy: A Prospective Study in 28 Patients," *Clin. Gen. Cancer*, vol. 12, No. 2, pp. 106-110 (2014).

Nanni, C. et al., "18F-Fluciclovine PET/CT for the Detection of Prostate Cancer Relapse. A Comparison to 11C-Choline PET/CT", *Clinical Nuclear Medicine*, vol. 40, No. 8, pp. e386-e391 (2015).

Nye, J. et al., "Biodistribution and Radiation Dosimetry of the Synthetic Nonmetabolized Amino Acid Analogue Anti-$^{18}$F-FACBC in Humans," J. Nucl. Med., vol. 48, pp. 1017-1020 (2007).

Odewole, O. et al., "Reproducibility and Reliability of Anti-3-[$^{18}$F]FACBC Uptake Measurements in Background Structures and Malignant Lesions on Follow-Up PET-CT in Prostate Carcinoma: an Exploratory Analysis," *Mol. Imaging Biol.*, vol. 17, pp. 277-283 (2015).

Oka, S. et al., "A Preliminary Study of Anti-1-Amino-3-$^{18}$F-Fluorocyclobuty1-1-Carboxylic Acid for the Detection of Prostate Cancer," *J. Nucl. Med.*, vol. 48, No. 1, pp. 46-55 (2007).

Oka, S. et al., "Transport Mechanisms of Trans-1-Amino-3-Fluoro [1-$^{14}$C]Cyclobutanecarboxylic Acid in Prostate Cancer Cells," *Nucl. Med. Biol.*, vol. 39, pp. 109-119 (2012).

Okamoto, S. et al., "Semiquantitative Analysis of C-11 Methionine PET May Distinguish Brain Tumor Recurrence from Radiation Necrosis Even in Small Lesions," *Ann. Nucl. Med.*, vol. 25, No. 3, pp. 213-220 (2011).

Okudaira, H. et al., "Putative Transport Mechanism and Intracellular Fate of Trans-1-Amino-3-$^{18}$F-Fluorocyclobutanecarboxylic Acid in Human Prostate Cancer," *J. Nucl. Med.*, vol. 52, No. 5, pp. 822-829 (2011).

Okudaira, H. et al., "Kinetic Analyses of Trans-1-Amino-3-[$^{18}$F]Fluorocyclobutanecarboxylic Acid Transport in Xenopus Laevis Oocytes Expressing Human ASCT2 and SNAT2," *Nucl. Med. Biol.*, vol. 40, pp. 670-675 (2013).

Okudaira, H. et al., "Corrigendum to 'Kinetic Analyses of Trans-1-Amino-3-[18F]fluorocyclobutanecarboxylic Acid Transport in Xenopus Laevis Oocytes Expressing Human ASCT2 and SNAT2'," *Nucl. Med. Biol.*, vol. 42, pp. 513-514 (2015).

Owenius, R. et al., "SUV Ratio Analysis of [$^{18}$F]Fluciclovine PET Data from Prostate Cancer Patients with Bone Marrow as Reference Tissue Gives Quantitative Values with High Time-Stability which is Favorable for Whole-Body Imaging," *Eur. J. Nucl. Med. Mol. Imaging*, OP169, vol. 39, Suppl. 2, p. S185 (2012).

Rice, S. et al., "The Next Generation of Positron Emission Tomography Radiopharmaceuticals in Oncology", *Semin. Nucl. Med.*, vol. 41, No. 4, pp. 265-282 (2011).

Rossi, P. et al., "Molecular Imaging of Advanced Prostate Cancer," *Curr. Probl. Cancer*, vol. 39, pp. 29-32 (2015).

Sasajima, T. et al., "Trans-1-Amino-3-$^{18}$F-Fluorocyclobutanecarboxylic Acid (Anti-$^{18}$F-FACBC) is a Feasible Alternative to $^{11}$C-Methyl-L-Methionine and Magnetic Resonance Imaging for Monitoring Treatment Response in Gliomas," *Nucl. Med. Biol.*, vol. 40, pp. 808-815 (2013).

Satoh, T. et al., "Phase IIa Clinical Trial of a New PET Tracer NMK36 in Metastatic Prostate Cancer," *J. Urology*, MP12-08, vol. 191, Suppl. 4S, pp. e107-e108 (2014).

Savir-Baruch, B. et al., "Pilot Evaluation of Anti-1-Amino-2-[$^{18}$F]Fluorocyclopentane-1-carboxylic acid (anti-2-[$^{18}$F] FACPC) PET-CT in Recurrent Prostate Carcinoma," *Mol. Imaging Biol.*, vol. 13, No. 6, pp. 1272-1277 (2011).

Schiavina, R. et al., "$^{18}$F-FACBC Compared with $^{11}$C-Choline PET/CT in Patients with Biochemical Relapse After Radical Prostatectomy: A Prospective Study in 79 Patients," *Abs. Eur. Urology*, Suppl. 13, P092, p. 144 (2014).

Schiavina, R. et al., "First Case of $^{18}$F-FACBC PET/CT-Guided Salvage Retroperitoneal Lymph Node Dissection for Disease Relapse

(56) References Cited

OTHER PUBLICATIONS after Radical Prostatectomy for Prostate Cancer and Negative [11]C-Choline PET/CT: New Imaging Techniques May Expand Pioneering Approaches," *Urologia Internationalis*, vol. 92, pp. 242-245 (2014).
Schuster, D. et al., "Initial Experience with the Radiotracer Anti-1-Amino-3-[18]F-Fluorocyclobutane-1-Carboxylic. Acid with PET/CT in Prostate Carcinoma," *J. Nucl. Med.*, vol. 48, No. 1, pp. 56-63 (2007).
Schuster, D. et al., "Initial Experience with the Radiotracer Anti-1-Amino-3-[$^{18}$F]Fluorocyclobutane-1-Carboxylic Acid (Anti-[$^{18}$F]FACBC) with PET in Renal Carcinoma," *Mol. Imaging Biol.*, vol. 11, pp. 434-436 (2009).
Schuster, D. et al., "Detection of Recurrent Prostate Carcinoma with Anti-1-Amino-3-[18]F-Fluorocyclobutane-1-Carboxylic Acid PET/CT and [111]In-Capromab Pendetide SPECT/CT," *Radiology*, vol. 259, pp. 852-861 (2011).
Schuster, D. et al., "Histopathologic Correlation of Prostatic Adenocarcinoma on Radical Prostatectomy with Pre-Operative Anti-[18]F Fluorocyclobutyl-Carboxylic Acid Positron Emission Tomography/Computed Tomography," *Annual Meeting Abstracts*, 939, pp. 222A-223A (2011).
Schuster, D. et al., "Characterization of Primary Prostate Carcinoma by Anti-1-Amino-2-[$^{18}$F]Fluorocyclobutane-1-Carboxylic Acid (Anti-3-[$^{18}$F]FACBC) Uptake," *Am J. Nucl. Med. Mol. Imaging*, vol. 3, No. 1, pp. 85-96 (2013).
Schuster, D. et al., "Anti-1-Amino-3-[18]F-Fluorocyclobutane-1-Carboxylic Acid: Physiologic Uptake Patterns, Incidental Findings, and Variants That May Simulate Disease, "*J. Nucl. Med.*, vol. 55, pp. 1986-1992 (2014).
Schuster, D. et al., "Anti-3-[$^{18}$F]FACBC Positron Emission Tomography-Computerized Tomography and [111]In-Capromab Pendetide Single Photon Emission Computerized Tomography-Computerized Tomography for Recurrent Prostate Carcinoma: Results of a Prospective Clinical Trial," *J. Urology*, vol. 191, No. 5, pp. 1446-1453 (2014).
Shepherd, T. et al., "Gaussian Process Models of Dynamic PET for Functional Volume Definition in Radiation Oncology," *IEEE Transactions on Medical Imaging*, vol. 31, No. 8, pp. 1542-1556 (2012).
Shoup, T. et al., "Synthesis and Evaluation of [$^{18}$F] 1-Amino-3-Fluorocyclobutane-1-Carboxylic Acid to Image Brain Tumors," *J. Nucl. Med.*, vol. 40, pp. 331-338 (1999).
Shreve, P. et al., "Metastatic Prostate Cancer: Initial Findings of PET with 2-Deoxy-2-[F-18]Fluoro-D-glucose," *Radiology*, vol. 199, pp. 751-756 (1996).
Simmons, M. et al., "Natural History of Biochemical Recurrence after Radical Prostatectomy: Risk Assessment for Secondary Therapy," *Eur. Urology*, vol. 51, pp. 1175-1184 (2007).
Sörensen, J. et al., "Regional Distribution and Kinetics of [$^{18}$F]Fluciclovine (anti-[$^{18}$F]FACBC), a Tracer of Amino. Acid Transport, in Subjects with Primary Prostate Cancer," *Eur. J. Nucl. Med. Mol. Imaging*, vol. 40, No. 3, pp. 394-402 (2013); published online Dec. 4, 2012.
Surti, S. et al., "Impact of TOF PET on Whole-body Oncologic Studies: a Human Observer Lesion Detection and Localization Study," *J. Nucl. Med.*, vol. 52, No. 5, pp. 712-719 (2011).
Strauss, L. et al., "The Applications of PET in Clinical Oncology," *J. Nucl. Med.*, vol. 32, pp. 623-648 (1991).
Turkbey, B. et al., "Prostate Cancer: Value of Multiparametric MR Imaging at 3 T for Detection—Histopathologic Correlation," *Radiology*, vol. 255, No. 1, pp. 89-99 (2010).
Turkbey, B. et al., "Prostate Cancer: Can Multiparametric MR Imaging Help Identify Patients Who are Candidates for Active Surveillance?" *Radiology*, vol. 268, No. 1, pp. 144-152 (2013).
Turkbey, B. et al., "Localized Prostate Cancer Detection with '[18]F FACBC PET/CT: Comparison with MR Imaging and Histopathologic Analysis," *Radiology*, vol. 270, No. 3, pp. 849-856 (2014).
U.S. Food and Drug Administration, "Review of F-18 Fluoro-2-Deoxyglucose (F-18 FDG) Positron Emission Tomography in the Evaluation of Malignancy," Aug. 4, 1999.

Wang, L. et al., "Synthesis and Evaluation of [18]F Labeled FET Prodrugs for Tumor Imaging," *Nucl. Med. Biol.*, vol. 41, No. 1, pp. 58-67 (2014).
Wang, Q. et al., "Targeting Amino Acid Transport in Metastatic Castration-resistant Prostate Cancer: Effects on Cell Cycle, Cell Growth, and Tumor Development," *J. National Cancer Institute*, vol. 105, No. 19, pp. 1463-1473 (2013).
Washburn, L. et al., "1-Aminocyclobutane[$^{11}$C] Carboxylic Acid, a Potential Tumor-Seeking Agent," *J. Nucl. Med.*, vol. 20, No. 10, pp. 1055-1061 (1979).
Yamaguchi, T. et al., "Prostate Cancer: a Comparative Study of [11]C-Choline PET and MR Imaging Combined with Proton MR Spectroscopy," *Eur. J. Nucl. Med. Mol. Imaging*, vol. 32, pp. 742-748 (2005).
Yu, C. et al., "Comparative Performance of PET Tracers in Biochemical Recurrence of Prostate Cancer: a Critical Analysis of Literature," *Am. J. Nucl. Med. Mol. Imaging*, vol. 4, No. 6, pp. 580-601 (2014).
Zanoni, L. et al., "[18]F-FACBC PET/CT for the Detection of Prostate Cancer Relapse: A Comparison to [11]C-Choline PET/CT," *Eur. Assoc. Nucl. Med. Congress* 2014, Gothenburg, abstract (2014) (2 pages).
Dénomination du medicadament: FLUOROCHOL 222 MBq/mL Solution Injectable, Chlorure de fluorocholine (18F), Feb. 18, 2016 (6 pages).
Prescribing information choline C 11 injection, Sep. 2012 (10 pages).
Prescribing information for sodium fluoride F18 injection, Oct. 2014 (10 pages).
Prescribing information for Axumin (fluciclovine F18) injection, May 2016, available at https://www.accessdata.fda.gov/drugsatfda_docs/label/2016/208054s000lbl.pdf (8 pages).
Cambridge Dictionary, definition of "sip," available at https://dictionary.cambridge.org/us/dictionary/english/sip, accessed Oct. 1, 2020 (8 pages).
Collins Dictionary, definition of "sip," available at https://www.collinsdictionary.com/us/dictionary/english/sip, accessed Oct. 1, 2020 (8 pages).
Crow, F.M., "Final days at home," *Canadian Family Physician*, vol. 60, pp. 543-545 (Jun. 2014).
LINX® Reflux Management System Instructions for Use and Patient Information, Mar. 2012 (36 pages).
Mercer, M., *Medication Training*, North Dakota Center for Persons with Disabilities, Mar. 2016 (96 pages).
Merriam-Webster Dictionary, definition of "sip", available at https://www.merriam-webster.com/dictionary/sip, accessed Oct. 1, 2020 (8 pages).
Ohio Gastroenterology Group, Inc., "Preparing for your EGD" (Sep. 2013) (1 page).
Oxford Dictionary, Lexico, definition of "sip," available at https://www.lexico.com/en/definition/sip, accessed Oct. 1, 2020 (4 pages).
Prescribing information for PROTONIX (pantoprazole sodium) delayed-release tablets, for oral use, Dec. 2014 (34 pages).
Prescribing information for SPRITAM (levetiracetam) tablets, for oral suspension, Jun. 2017 (38 pages).
Singata, M. et al., "Restricting oral fluid and food intake during labour," *Cochrane Database Syst. Rev.*, pp. 1-59 (Sep. 2014).
Sweeney, R.M. et al., "Perioperative Intravenous Fluid Therapy for Adults," *Ulster. Med. J.*, vol. 82, No. 3, pp. 171-178 (2013).
Gardner, F. et al., "Male Choriocarcinoma with Pulmonary and Liver Metastases, Choriocarcinoma Syndrome, and Brain Metastasis: a Case Report and Review of the Literature," *Ann. Hematol. Oncol.*, vol. 1, pp. 1-3 (Sep. 2014).
Glore, R.J. et al., "A patient with thy mouth," *Clinical Otolaryngology*, vol. 34, pp. 358-363 (2009).
Parent, E.E. et al., "Update on [18]F-Fluciclovine PET for Prostate Cancer Imaging," *J. Nucl. Med.*, vol. 59, pp. 733-739 (May 2018).
Senthilkumaran, S. et al., "Ageusia following cobra envenomation: Myth and fact on venom sucking," *Int. J. of Case Reports and Images*, vol. 2, pp. 1-5 (Apr. 2011).
"Typical Preoperative Order Sheet," Appendix 1 in Bojar, R.M., *Manual of Perioperative Care in Adult Cardiac Surgery*, Fourth Edition, Wiley-Blackwell (2005) (2 pages).

Fluciclovine (18F) PET/CT
Pre-Therapy
Transaxial slice

Fluciclovine (18F) PET/CT
Post-Therapy
Transaxial slice

IMAGING OF METASTATIC OR RECURRENT CANCER

CROSS-REFERENCE TO RELATED APPLICATIONS

This application is a continuation of U.S. application Ser. No. 16/160,227 filed on Oct. 15, 2018, now U.S. Pat. No. 10,716,868, which is a continuation of U.S. application Ser. No. 14/983,746 filed on Dec. 30, 2015, now U.S. Pat. No. 10,124,079, each of which is incorporated by reference herein in its entirety.

FIELD OF THE DISCLOSURE

The present disclosure relates to methods of administering [$^{18}$F]-FACBC. The present disclosure also relates to use of [$^{18}$F]-FACBC in methods for imaging, diagnosing and monitoring metastasis or recurrence of cancer.

BACKGROUND

Fluciclovine ($^{18}$F) injection, also known as [$^{18}$F]-FACBC, FACBC, or anti-1-amino-3-$^{18}$F-fluorocyclobutane-1-carboxylic acid, is a synthetic amino acid imaging agent which is taken up specifically by amino acid transporters and is used for positron emission tomography (PET). PET is uniquely suited to evaluate metabolic activity in human tissue for diagnostic imaging purposes. [$^{18}$F]-fluoro-2-deoxy-glucose (FDG) is a PET imaging agent for the detection and localisation of many forms of cancer. However, FDG-PET has been found to have less sensitivity and/or specificity for assessment of some types of cancer, for example, prostate cancer. [$^{18}$F]-FACBC on the other hand shows great promise in the imaging of a variety of cancers including primary and recurrent prostate cancer, as it has excellent in vitro uptake and low urinary excretion. PET imaging with [$^{18}$F]-FACBC better defines tumours compared to other known tracers such as FDG, allowing for better diagnosis and planning of treatment, for example, by directing radiation therapy to the appropriate areas.

Metastasis involves a complex series of steps in which cancer cells leave the original tumour site and migrate to other parts of the body via the bloodstream or the lymphatic system. The new occurrences of tumour thus generated are referred to as a metastatic tumour or metastasis. Metastatic tumours are very common in the late stages of cancer and are a major cause of death from solid tumours. Until now, [$^{18}$F]-FACBC has not been reported as being used in the monitoring of metastatic cancer. There are known difficulties associated with diagnosing and monitoring metastatic cancer, for example, obtaining two or more images at different time points with enough accuracy to enable comparison is challenging.

Thus there is a need for a method of imaging which allows for reproducible, reliable imaging for detection and monitoring of metastatic cancer.

SUMMARY

The present disclosure relates to methods of administering [$^{18}$F]-FACBC for improved PET imaging and more reliable diagnosis of metastasis or cancer reoccurrence. The disclosure further relates to a method of diagnosing metastasis or cancer reoccurrence using the PET imaging agent [$^{18}$F]-FACBC.

In an aspect of the disclosure, there is provided a method of administering [$^{18}$F]-FACBC to a subject comprising the steps of:
  a) injecting a detectable amount of [$^{18}$F]-FACBC into the right arm of a subject, wherein said arm is positioned adjacent to the subject's torso;
  b) raising said arm in to an overhead position;
  c) acquiring a PET scan image of the subject;
wherein said arm remains in the overhead position during the PET scan.

In at least one embodiment, step c), i.e. image acquisition, starts about 3 to 5 minutes after an injection of [$^{18}$F]-FACBC has been administered, optionally 4 minutes after the end of the injection.

In a further aspect there is provided a method of imaging metastatic or recurrent cancer in a subject, comprising the steps of:
  a) administering to the subject a first dose of a detectable amount of [$^{18}$F]-FACBC and allowing time for the [$^{18}$F]-FACBC to accumulate at one or more areas of interest within the subject;
  b) obtaining a first PET scan image of the subject;
  c) administering to the subject a second dose of a detectable amount of [$^{18}$F]-FACBC and allowing time for [$^{18}$F]-FACBC to accumulate at one or more areas of interest within the subject;
  d) obtaining a second PET scan image of the subject;
wherein the first and second scan images indicate the location and intensity of [$^{18}$F]-FACBC and wherein localisation of [$^{18}$F]-FACBC indicates the presence of tumour tissue in the subject.

In one aspect there is provided a method of diagnosing or monitoring metastatic or recurrent cancer in a subject, comprising the steps of:
  a) administering to the subject a first dose of a detectable amount of [$^{18}$F]-FACBC and allowing time for the [$^{18}$F]-FACBC to accumulate at one or more areas of interest within the subject;
  b) obtaining a first PET scan image of the subject, wherein the scan image indicates the location and intensity of [$^{18}$F]-FACBC;
  c) administering to the subject a second dose of a detectable amount of [$^{18}$F]-FACBC and allowing time for [$^{18}$F]-FACBC to accumulate at one or more areas of interest within the subject;
  d) obtaining a second PET scan image of the subject, wherein the scan image indicates the location and intensity of [$^{18}$F]-FACBC;
  e) comparing the first and second scan images to determine whether the location and/or intensity of [$^{18}$F]-FACBC has increased, remained constant, or decreased, thereby diagnosing or monitoring metastatic or recurrent cancer in a subject.

In at least one embodiment of the second or third aspect, both PET and magnetic resonance imaging (MRI) or x-ray computed tomography (CT) scan images are acquired in steps b) and d), for example, by use of a combined PET-MRI or PET-CT system.

In an aspect of the disclosure there is provided a method of imaging metastatic cancer in a subject, comprising i) administering [$^{18}$F]-FACBC to a subject according to the first aspect; and ii) imaging the subject according to the second aspect.

In another aspect, scanning is performed according to the following parameters:
  i) scanning starts 3 to 5 minutes after administration of [$^{18}$F]-FACBC, optionally about 4 minutes after administration of [$^{18}$F]-FACBC;
  ii) scanning takes place in the direction of feet to head;
  iii) for the first 2 or 3 bed positions, the scanning time per bed position is of 4 to 5 minutes;
  iv) for the subsequent bed positions, the scanning time per bed position is of 2 to 3 minutes.

In at least one further embodiment, scanning starts at the proximal thigh. The scan may continue to the base of the skull.

In at least one further embodiment, scanning is completed within 30 minutes of administration of [$^{18}$F]-FACBC, which is the period during which the signal to noise ratio is the highest.

Advantages and improvements associated with the administration protocol described herein may include one or more of the following:
  i) early imaging starting ~4 min after injection
  ii) starting at base of pelvis and working up,
  iii) imaging for longer times/bed (4-5 mins) for the first 2-3 bed positions and then reverting to shorter times per bed (2-3 min).

What may be achieved clinically according to some embodiments of the present disclosure is sensitive detection of prostate cancer recurrence in practical imaging times. There are several factors at play which to a certain extent may compete with each other:
a) Disease spreads from the prostate/prostate bed generally upwards to pelvic nodes, retroperitoneal nodes, pelvic bones or lumbar spine and then to more superior (higher up) locations. Thus, it may make sense to look 'harder' in these inferior (lower down) regions where disease spread is more likely rather than higher up.
b) Signal to noise for FACBC may be highest at time after injection of ~4 to 20-30 mins
c) Imaging for longer times per bed can lead to better detection of small lesions
d) It may be beneficial to get through at least 2 patients an hour per scanner in routine use.

Aspects of the present disclosure may balance one or more of these factors, e.g., in order to achieve a more time and cost efficient process.

In another aspect of the disclosure there is provided a method of diagnosing or monitoring metastatic cancer in a subject, comprising i) administering [$^{18}$F]-FACBC to a subject using an administration protocol as described herein; and ii) diagnosing or monitoring metastatic cancer.

In a further aspect there is provided a kit for imaging, diagnosing or monitoring metastatic cancer, comprising: a) [$^{18}$F]-FACBC tracer; b) administration instructions according to the first aspect.

In an aspect of the disclosure there is provided the acquisition of images using a PET/MRI or PET/CT scanner. The simultaneous or consecutive acquisition of images on a PET/MRI or PET/CT scanner may, for example, offer improved diagnostic accuracy over the generation of images on separate instruments. The conjoint use with MRI may improve the localisation of tumours, particularly where the tumours are small, for example in the case of metastatic tumours. The method of administration can be embodiments of the method described herein.

DESCRIPTION OF THE DRAWINGS

FIG. 1b shows stasis of tracer (circled). High 'uptake' of fluciclovine is demonstrated by the high standardized uptake value (SUV) of >200 in the anatomical region normally associated with a Virchow-Troisier's Node.

DETAILED DESCRIPTION

The present inventors have established a protocol which may allow for the reliable imaging of metastatic cancer, e.g., allowing the data from PET scan images to be analysed and compared in order to accurately diagnose and/or monitor metastatic cancer.

The terms "approximately" and "about" refer to being nearly the same as a referenced number or value. As used herein, the terms "approximately" and "about" generally should be understood to encompass ±5% of a specified amount or value.

Disclosed is a method of detecting tumours in a patient comprising administering [$^{18}$F]-FACBC to a subject and imaging the subject on a PET/MRI or PET/CT scanner to obtain conjoint PET and MRI images or PET and CT images. The tumours may be metastatic tumours. The administration and/or PET imaging methods may be as described below.

In an aspect of the disclosure, there is provided a method of administering [$^{18}$F]-FACBC to a subject comprising the steps of:
  a) injecting a detectable amount of [$^{18}$F]-FACBC into the right arm of a subject, wherein said arm is positioned adjacent to the subject's torso;
  b) raising said arm in to an overhead position;
  c) acquiring a PET scan image of the subject;
wherein said arm remains in the overhead position during the PET scan.

Figure 1A:
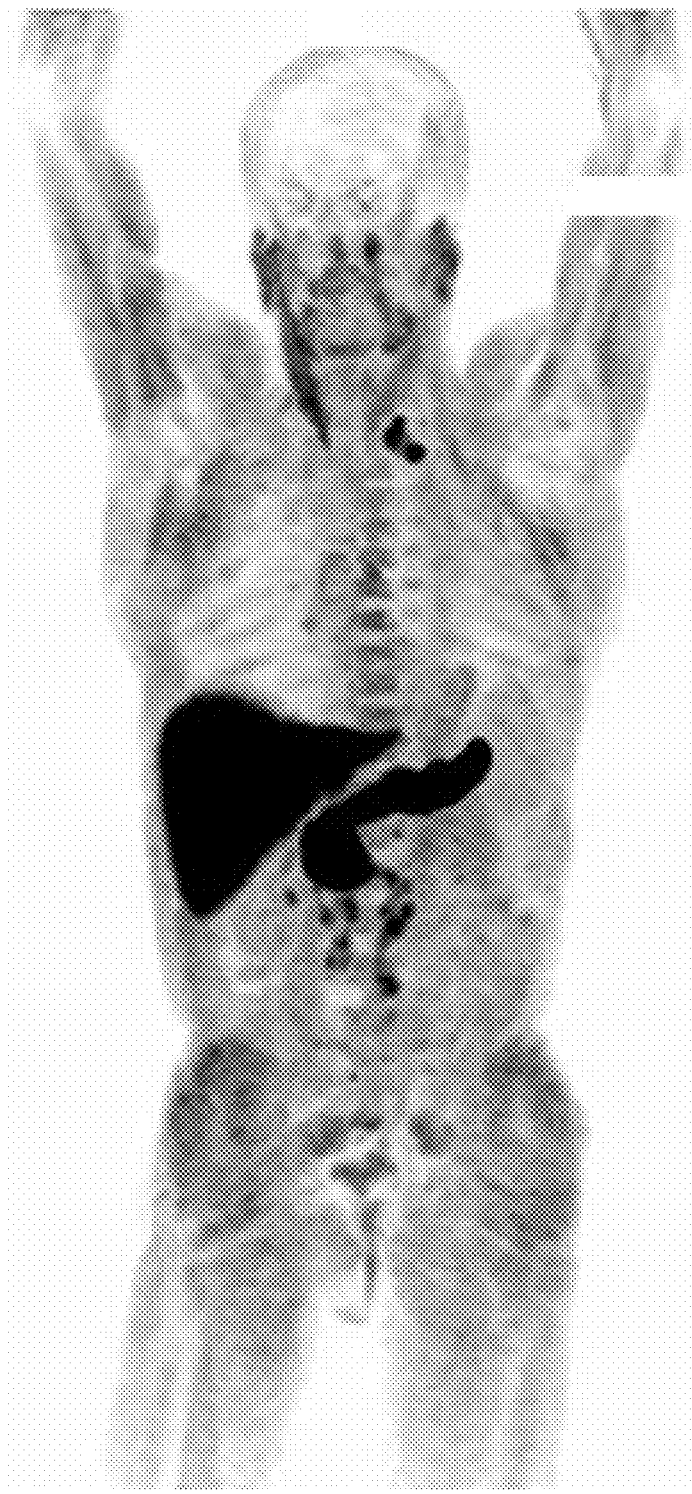
FIGS. 1a and 1b show accumulation of FACBC in the Virchow's node when the FACBC is injected into the left arm.
Figure 1B:
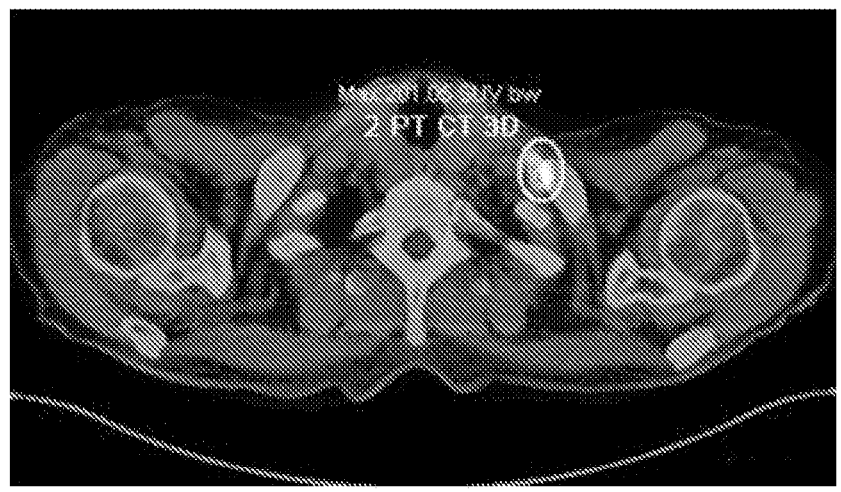

In some embodiments, the right arm may be preferred as stasis in the axillary vein upon injection in the left arm may be misinterpreted as a metastatic lymph node called Virchow's node, which is located in the left supraclavicular fossa (the area above the left clavicle, or collar bone). For example, FIGS. 1a and 1b show accumulation of FACBC in the Virchow's node when the FACBC is injected into the left arm. FIG. 1b shows stasis of tracer (circled). In this example, high 'uptake' of fluciclovine is demonstrated by the high standardized uptake value (SUV) of >200 in the anatomical region normally associated with a Virchow-Troisier's Node.

In step a), [$^{18}$F]-FACBC is optionally injected over a time period of about 1 to 2 minutes, for example over about 1 minute. A relatively slow injection bolus may be beneficial, e.g., because of a risk of a systemic reaction due to the relatively low pH dose striking the left ventricle. [$^{18}$F]-FACBC may be injected by any suitable means in order for it to enter the bloodstream and/or the lymphatic system. Optionally, the injection is an intravenous injection. The injection can be followed by a flush of about 10 mL or less.

In some embodiments, immediately after injection, for example less than about 10 seconds, less than about 5 seconds, or less about 2 seconds after the end of the injection, the subject's arm is raised to an overhead position prior to image acquisition. Optionally injection takes place whilst the subject is lying down in a horizontal position with both arms adjacent to the subject's torso, and immediately after injection both arms are raised into the overhead position prior to image acquisition.

Amino acids are important nutrients for tumour growth. After injection, tumour cells may uptake [$^{18}$F]-FACBC and the cells which have taken up the tracer can be subsequently visualised. Acquisition can start 3 to 5 minutes after the end of the injection, optionally 4 minutes after the end of the injection. [$^{18}$F]-FACBC may be taken up by tumour cells relatively quickly compared to other PET radiotracers with different uptake mechanisms. For example, In FDG-PET imaging, acquisition usually starts at least 45 minutes after injection.

A "detectable amount" of [$^{18}$F]-FACBC refers to a dosage of [$^{18}$F]-FACBC which is taken up by tumour cells allowing those cells to be detected by PET imaging. Optionally the dosage of [$^{18}$F]-FACBC is between 250 and 500 MBq, for example between 290 and 450 MBq, for example 370±20% MBq. The dosage may be diluted up to 10 mL.

Figure 2:
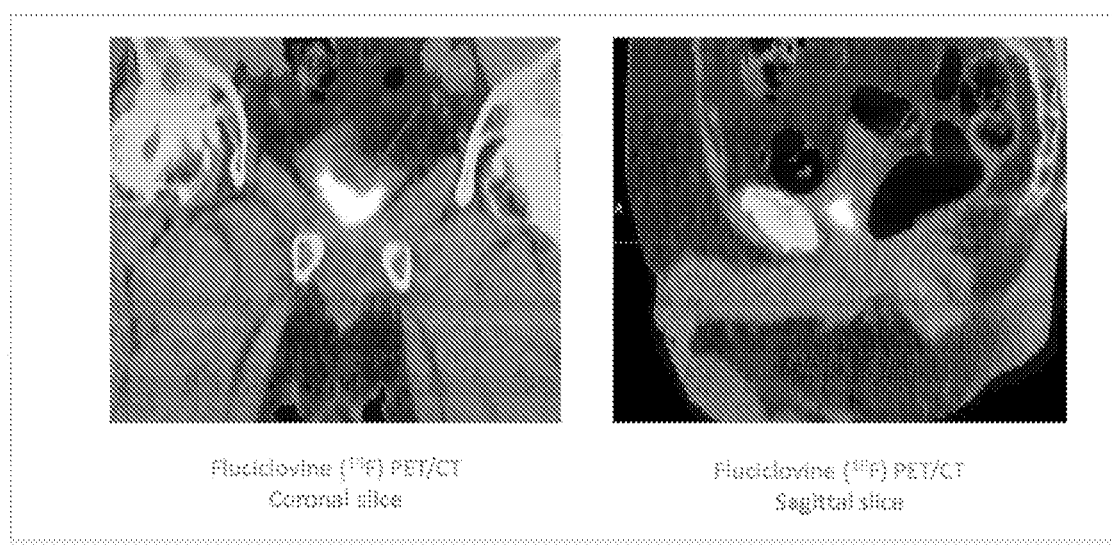
FIG. 2 shows images from an example where FACBC accumulated in the bladder as the patient was over-hydrated. In this example, significant urine in the bladder, shown as a solid arrow, means that the prostate bed (inferior to the bladder) cannot be visualized.

Optionally the patient fasts for at least 4 hours, for example 4 to 6 hours, prior to administration of [$^{18}$F]-FACBC. The term 'fast' means to consume no food or drink. For example, only sips of water may be consumed within the 4 hours prior to administration if needed for the administration of medications. The consumption of water prior to [$^{18}$F]-FACBC uptake may cause activity in urine in the bladder which may challenge readings of images of the pelvic region. FIG. 2 shows exemplary images where FACBC has accumulated in the bladder as the patient is over-hydrated. In this example, significant urine in the bladder, shown as a solid arrow, means that the prostate bed (inferior to the bladder) cannot be visualized.

Optionally the patient avoids exercise a day before the scan through to the time of the scan. Exercising may increase the demand by muscle tissue for amino acids, which may result in general muscle uptake of the [$^{18}$F]-FACBC tracer and can lead to unreliable readings.

The PET imaging technique utilises scanning devices that detect the 511 keV annihilation photons that are emitted after radioactive decay of fluorine-18. PET scanners are generally available for imaging of human subjects. In addition, "micro-PET" scanners that have high spatial resolution can be used for imaging of small animals. In addition to PET scanners, $^{18}$F-radioactivity can also be monitored using one or more radiation detector probes.

In another aspect there is provided a method of imaging metastatic cancer in a subject, comprising the steps of:
 a) administering to the subject a first dose of a detectable amount of [$^{18}$F]-FACBC and allowing time for the [$^{18}$F]-FACBC to accumulate at one or more areas of interest within the subject;
 b) obtaining a first PET scan image of the subject;
 c) administering to the subject a second dose of a detectable amount of [$^{18}$F]-FACBC and allowing time for [$^{18}$F]-FACBC to accumulate at one or more areas of interest within the subject;
 d) obtaining a second PET scan image of the subject;
 wherein the first and second scan images indicate the location and intensity of [$^{18}$F]-FACBC and wherein localisation of [$^{18}$F]-FACBC indicates the presence of tumour tissue in the subject.

In a further aspect there is provided a method of diagnosing or monitoring metastatic cancer in a subject, comprising the steps of:
 a) administering to the subject a first dose of a detectable amount of [$^{18}$F]-FACBC and allowing time for the [$^{18}$F]-FACBC to accumulate at one or more areas of interest within the subject;
 b) obtaining a first PET scan image of the subject, wherein the scan image indicates the location and intensity of [$^{18}$F]-FACBC;
 c) administering to the subject a second dose of a detectable amount of [$^{18}$F]-FACBC and allowing time for [$^{18}$F]-FACBC to accumulate at one or more areas of interest within the subject;
 d) obtaining a second PET scan image of the subject, wherein the scan image indicates the location and intensity of [$^{18}$F]-FACBC;
 e) comparing the first and second scan images to determine whether the location and/or intensity of [$^{18}$F]-FACBC has increased, remained constant, or decreased.

In one embodiment of the second or third aspect, both PET and magnetic resonance imaging (MRI) or x-ray computed tomography (CT) scan images are acquired in steps b) and d), for example, by use of a combined PET-MRI or PET-CT system.

In at least one embodiment, [$^{18}$F]-FACBC is administered according to the first aspect of the present disclosure.

The time required for [$^{18}$F]-FACBC to accumulate in tumour cells in steps a) and c) of the aspects described above may be about 5 minutes or less after [$^{18}$F]-FACBC is administered. Optionally, the time taken for [$^{18}$F]-FACBC to accumulate is 3 to 5 minutes, for example 4 minutes. This therefore allows image acquisition to start 3 to 5 minutes after administration, for example 4 minutes after [$^{18}$F]-FACBC administration.

Figure 3:
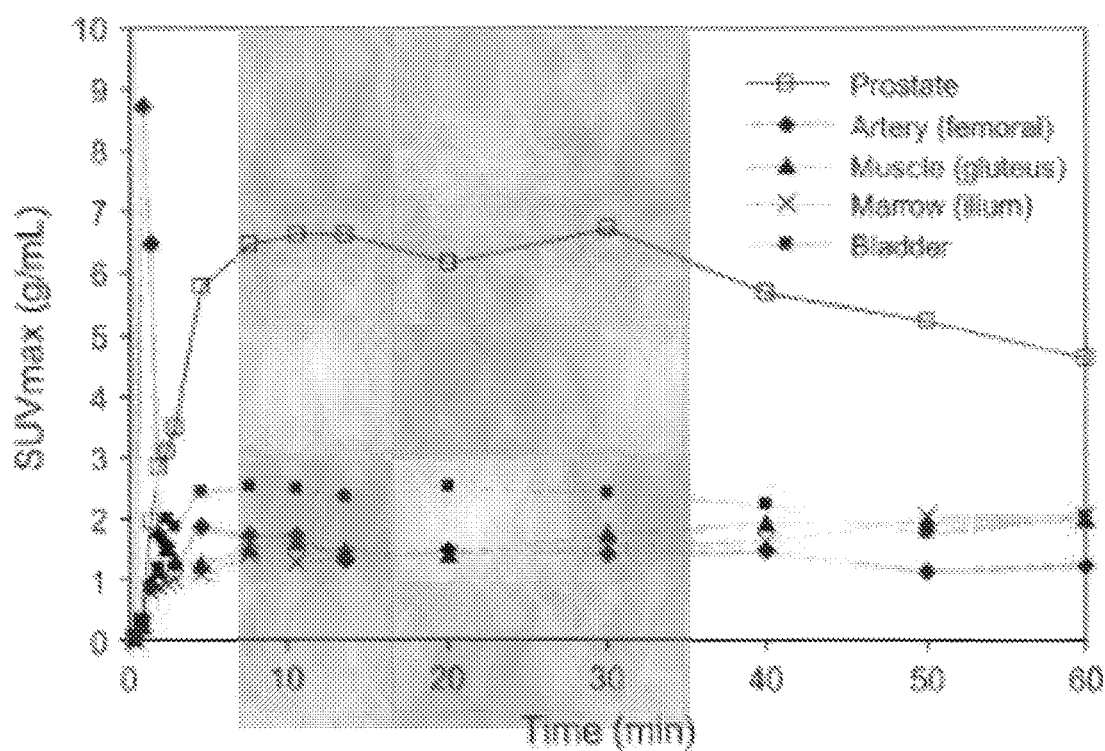
FIG. 3 illustrates exemplary time activity curves showing rapid uptake of fluciclovine (18F) in known prostate carcinoma recurrence, to a maximum at 4.5 minutes with a plateau to 30 minutes, which is followed by gradual clearance (9%/min) out to 60 minutes. Regions in marrow (ilium), muscle (gluteus), and bladder reached a plateau at 4.5 minutes that remained constant throughout the imaging period.

FIG. 3 illustrates exemplary time activity curves showing rapid uptake of fluciclovine ($^{18}$F) in known prostate carcinoma recurrence, to a maximum at 4.5 minutes with a plateau to 30 minutes, which is followed by gradual clearance (9%/min) out to 60 minutes. Regions in marrow (ilium), muscle (gluteus), and bladder reached a plateau at 4.5 minutes that remained constant throughout the imaging period.

During the PET scan the patient is optionally in the supine position and scanning takes place in the direction of feet to head. The start and end positions of the scan may vary depending on the region of interest. Starting the scan at the proximal thigh and scanning to the base of the skull may capture the majority of lesions.

Once data has been collected from the first PET scan, the images can be visualised and used to view the volume, shape and/or location of tumour cells within the subject. Images may be visually interpreted by a nuclear medicine physician or radiologist and standardised uptake values (SUVs) such as SUVmax and SUVmean may be determined.

In at least another aspect, scanning is performed according to the following parameters:
i) scanning starts 3 to 5 minutes after administration of [$^{18}$F]-FACBC, optionally about 4 minutes after administration of [$^{18}$F]-FACBC;
ii) scanning takes place in the direction of feet to head;
iii) for the first 2 or 3 bed positions, the scanning time per bed position is of 4 to 5 minutes;
iv) for the subsequent bed positions, the scanning time per bed position is of 2 to 3 minutes.

In at least one embodiment, scanning starts at the proximal thigh to the base of the skull.

In at least one embodiment, scanning is performed between 3 to 30 minutes after administration of [$^{18}$F]-FACBC, which may be the period during which the signal to noise ratio is the highest.

The time between acquisition of the first and second PET scan images, i.e. between steps b) and d) of the aspects described above may be as much as one year. In some instances, the time between the first and second PET scans may be about 6 months, 5 months, 4 months, 3 months, 2 months, 1 month or even less than about 1 month. It will be appreciated that steps c) and d) of the second and third aspects described above may be repeated as many times as desired and/or necessary in order to obtain multiple scan images which can be used to map the development of a tumour over time.

Once image data has been collected from the second PET scan, the first and second images may be visualised together and used to view the change in extent and location of tumour cells within the subject, allowing for the diagnosis or monitoring of metastatic or recurrent cancer. For example, if the location of the tumour cells has changed then the subject may be diagnosed with metastatic cancer. In some embodiments, the second scan image can be compared to images of data collected from an earlier PET scan taken before the first PET scan, in addition to comparison with the first PET scan. In addition, any subsequent PET scan images obtained after the second PET scan image can be compared with the first and/or second PET scan images.

Figure 4:
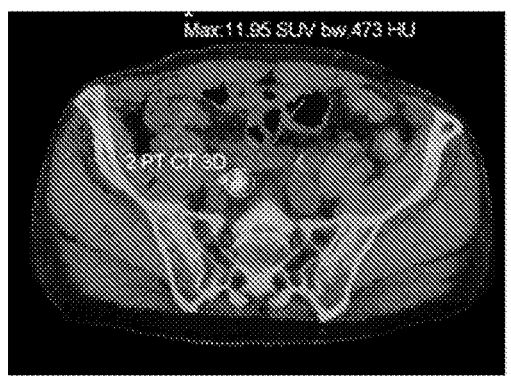
FIG. 4 shows exemplary images before and after treatment for prostate cancer. Significant quantitative decrease in fluciclovine (18F) uptake post therapy were seen showing that images taken at different time points can be compared (solid arrows).
Figure 4:
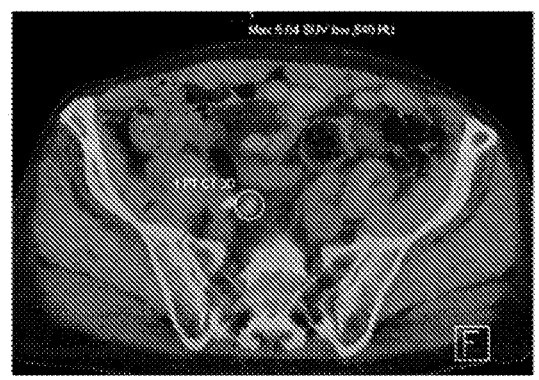

By comparing the images from two or more differing time points, the differences in the tumour uptake of [$^{18}$F]-FACBC can be analysed. Comparisons can involve qualitative image comparison (e.g., contrast of tumour uptake from background) and/or quantitative indices derived from the imaging or external radiation detection data (e.g., SUVs). The development, progression or reduction of any tumours can therefore be monitored and diagnosed accordingly. Suitable treatment can then be determined, for example, targeted administration of localised treatment at the site of the tumour. It will be appreciated that the methods described herein can also be used to monitor response to various therapeutic regimens, including chemotherapy. FIG. 4 shows exemplary images before and after treatment for prostate cancer. Significant quantitative decrease in fluciclovine ($^{18}$F) uptake post therapy were seen showing that images taken at different time points can be compared (solid arrows).

The PET scan image obtained in steps b) and d) of the methods described above may be combined with, preceded or followed by anatomical imaging selected from computed tomography (CT) imaging, computerized axial tomography (CAT) imaging, MRI imaging ultrasound, or a combination thereof. For combined imaging, the images can be acquired using a dedicated PET-CT, PET-MRI, PET-ultrasound scanning device or separate PET and CT/MRI/ultrasound scanning devices. If separate PET and CT/MRI/ultrasound imaging devices are used, image analysis techniques can be employed to spatially register the PET images with the anatomical images.

In at least one embodiment, the image acquisition steps b) and d) involve obtaining a combined PET scan image and MRI scan image. The PET-MRI images can be obtained using a dedicated PET-MRI scanning device. Such scanning devices are available from Siemens (Biograph mMR) and GE (SIGNA PET/MR). Since MRI does not use any ionizing radiation, its use generally may be favoured in preference to CT in some instances. An advantage of PET-MRI acquisition may be that the patient and medical staff only need to be present for a single scan resulting in a more time and cost efficient process.

In at least another embodiment, the image acquisition steps b) and d) involve obtaining a combined PET scan image and CT scan image. The PET-CT images can be obtained using a dedicated PET-CT scanning device. An advantage of PET-CT acquisition may be that the patient and medical staff only need to be present for a single scan resulting in a more time and cost efficient process.

The methods described herein can be used for intra-organ mapping of tumour location, for example, the spatial distribution of prostate carcinoma within the prostate gland can be determined for aiding in biopsy of the prostate gland or planning of radiation therapy of the prostate gland either by external beam radiation or brachytherapy. Likewise, the method may be used for guiding the biopsy or surgical resection of lymph nodes.

The methods described herein are intended to be suitable for detecting metastasis formation derived from primary prostate tumours. [$^{18}$F]-FACBC can be used in the detection and localisation of a wide variety of metastatic cancers. [$^{18}$F]-FACBC may be particularly useful for imaging pelvic tumours, and metastases thereof in the pelvic lymph nodes.

In at least one embodiment, the methods of the disclosure are used to diagnose metastatic prostate cancer.

The methods described herein may be suitable for detecting recurrence of prostate cancer. [$^{18}$F]-FACBC may be particularly useful for imaging pelvic tumours, including prostate tumours and recurrence thereof in the pelvic lymph nodes.

In at least one embodiment, the methods of the disclosure are used to diagnose recurrent prostate cancer.

The methods of the present disclosure may be used in humans and/or may be used in non-human animals (for example, dogs and cats).

Another aspect of the disclosure provides a kit for imaging, diagnosing or monitoring metastatic cancer, comprising: a) [$^{18}$F]-FACBC tracer; b) administration instructions in accordance with the first aspect.

The following examples are intended to illustrate aspects of the present disclosure without, however, being limiting in nature. It is understood that the present disclosure encompasses additional embodiments consistent with the foregoing description and following examples.

EXAMPLES

Investigators from 3 different patient imaging sites were asked to select 8 fluciclovine scans/cases from their past studies. The sites were asked to select cases that covered a range of findings from subtle to obvious. The sites also submitted completed patient histories and unblinded read data that detailed the location of fluciclovine-avid lesions, SUVmax, reference tissue used in evaluating the lesion, target-to-reference tissue ratio, and the confidence rating of the positive finding. The overall impression of level of confidence of disease in the prostate bed and in extraprostatic areas was rated as Probably Negative, Probably Positive, or Confirmed Positive (1—Negative, 2—Unlikely, 3—Equivocal, 4—Probable, 5—Definite). If Confirmed Positive was selected, the method(s) of confirmation, defined as Histopathology, Standard of Care Imaging, or Clinical Follow-up, were to be selected.

The image acquisition and interpretation parameters and scanner information were compiled and presented in table format. Differences in acquisition parameters existed in the use of contrast, superior extent of the scan, minutes per bed position, acquisition of delayed images and hydration requirements. A summary of the data is presented below in Table 1:

that the dosage of fluciclovine (370±20% MBq) should ideally be diluted up to 10 mL and injected into the right arm, when possible, with the arms down and a slow push over 1 minute followed by ≥10 mL flush.

The right arm is preferred as stasis in axillary vein may be misinterpreted as a metastatic lymph node (Virchow's node). The arms should be moved back to the scanning overhead position following the dosage and flush. Imaging should begin at 3 to 5 minutes with a goal of 4 minutes from the end of the injection.

All sites scanned patients in the supine position in the direction of feet to head; however, the start and end positions of the scan itself varied. The group agreed that starting the scan at the proximal thigh and scanning to the base of the skull would capture the vast majority of the lesions. Inves-

TABLE 1

Image Acquisition

| Scanner(s) | GE Discovery STE | GE Discovery DLS | GE 690 | Siemens mCT Biograph 40 | GE 690 |
|---|---|---|---|---|---|
| Acquisition mode | 3D | 2D | 3D | 3D | 3D |
| Attenuated CT | 80 mA, 120 kVp, 16 | 75-160 mA, 120 kVp | 75-160 mA, 120 kVp | 50 mA, 120 kVp | 300 mA, 120 kVp |
| Administered activity | 370 MBq | 370 MBq | 370 MBq | 200*-400 MBq *suboptimal | 3.5 MBq/kg |
| Contrast used? | No | Yes, oral | Yes, oral | No | Yes |
| Position: | Supine | Supine | Supine | Supine | Supine |
| Direction: | Feet first | Head first | Head first | Head first | Feet first |
| Arm Position | Behind head | Behind head | Behind head | Behind head | Behind head |
| Start Scan | Mid-femur | Symphysis pubis | Below Symphysis pubis | Proximal thigh | Pelvis, centered over prostate |
| End Scan | Top of skull | Above diaphragm | Above diaphragm | Vertex | Neck |
| Minutes per bed pos. | 2 | 4 | 3 | 2 | 2.5 min dynamic scan for 15 min |
| Number of bed pos. | 8-9 | 3 | 4 | 7 +/− 1 | 5-6 |
| Uptake time initial | 3 min | 5 min (end at 16) | 5 min (end at 16) | 5 min | 0 min |
| Uptake time second | N/A | 17 min (end at 28) | 17 min (end at 28) | N/A | N/A |
| Uptake time third | N/A | 29 min (end at 40) | 29 min (end at 40) | N/A | N/A |

It was noted that the patients who had activity in urine in the bladder were more difficult to interpret with urinary excretion potentially being confused with malignancy or smooth muscle uptake in urethra and unspecific uptake in the central zone. Dynamic uptake may possibly be useful to differentiate between unspecific urethral/central zone uptake and early urinary excretion. It had been the practice at some sites for patients to drink water prior to the injection of fluciclovine. The other sites did not prescribe hydration and had no issues with urine in the bladder. It was concluded that patients should fast for at least 4 hours prior to the scan, drinking only sips of water within 4 hours prior to the scan, if needed for administration of medications. Some patients demonstrated general muscle uptake of the tracer. In a number of patients, some muscles showed particularly high uptake, believed to be related to increased muscular activity, e.g., due to strenuous exercise. To avoid an increased demand by muscle tissue for amino acid, patients should not exercise from the day before the scan through to the time of the scan.

All sites injected the tracer with arms down, and immediately after the injection the arms were raised above the head to prepare for imaging. In some patients stasis of the tracer in the axillary vein was noted. The group concluded tigator A's scanning protocol was to scan to the dome of the diaphragm, then repeat a delayed scan starting again at the symphysis pubis at approximately minute 17. The group reviewed images from both time points and agreed that the initial scan provided the most useful data. Investigator D performed dynamic scanning for 15 minutes over the pelvis before finishing with static scans to the neck. The Investigator D images were rebinned into 3×5 minute blocks, thus 0-5, 5-10, and 10-15 minutes. The group reviewed all three time points. They agreed that the most useful images were in the 5-10 minutes window. While providing some interesting data points, data from the delayed and dynamic imaging sequences did not alter the result of the reads. This observation further supported the proposed standardized acquisition parameters. Thus it was concluded that for general clinical practice, patients should be imaged for a minimum of 3 minutes per bed position, extending to up to 5 minutes per bed position for the first two bed positions, in a single, static scan. Imaging should begin at 4 minutes after end of injection. For the CT parameters, a high-quality CT with no contrast for clinical studies, and a 3 mm maximum slice thickness should be employed. Contrast may be indicated in clinical trials.

Because of the known challenges with detection of small lesions in these patients, in general, the highest quality scanner at a site should be utilized. If a scanner has time-of-flight (TOF), iterative reconstruction and a reconstruction algorithm using recovery resolution, the features should be used. For quantitative assessment, the sites should reconstruct images using standardised reconstruction parameters specific to the scanner being utilised.

In interpreting the images, all sites agreed on measuring lymph node size on CT and SUVmean and SUVmax on PET. The background reference tissue varied by site between blood pool, surrounding tissue, and marrow of the L3 vertebrae. Following the collaborative read of all images, a read consensus was developed that details the background tissue reference to be used. The tissue reference is dependent on the type (i.e., prostate bed, lymph node), size, and location of the lesion.

Consensus Group Image Read and Interpretation

The cases reads were determined to be concordant or discordant. To be concordant, the blinded read had to match the unblinded read in all three areas (bed, lymph nodes, distant disease such as bone) in overall positive or negative for disease and, if positive, have disease noted in the same specific area (e.g., left para-aortic lymph node, right iliac bone, etc.).

Investigators used a 5-point scale to assess their confidence in the presence of positive findings. The scale was 1—Negative, 2—Unlikely, 3—Equivocal, 4—Probable, 5—Definite. A rating of 1 or 2 would be considered Probably Negative, a rating of 4 or 5 would be considered Probably Positive, and 3 would be equivocal. For the consensus group read, the 6 experienced readers plus the independent reader sat at one workstation to review the cases together (utilizing the Volume Viewer application on the GE Advantage workstation). The investigators rotated time at the controls of the reading station, narrating how they performed image review. They noted how they approached the images, including use of the maximum intensity projection (MIP), windowing, change of windowing during the reading, planes of view, use of colour tables, and comparison with background reference tissue. The preferred approaches of each were recorded and discussed after the first day of reading. Prior to reading cases on day 2, the group defined the approach they would use to review the cases. To start the review, readers used windowing procedures similar to ($^{18}$F) FDG methods. Initially, the PET window is set so the liver and pancreas are intense. The optimum window varies for different tissue types. Suggested windows are 0 to 10 SUV for bone marrow, 0 to 7 SUV for lymph nodes, and 0 to 15 SUV for liver (the precise appropriate windowing is scanner/workstation dependent). Multiple orthogonal planes (axial, saggital, and coronal) of view should be used. It was also noted that the MIP is useful for detecting lesions, especially in bone but also lymph nodes. Colour tables are a personal preference often based on the reading station and past experience.

The group reviewed the discordant cases that were identified from the paired reads. The review included an oral summary of the relevant patient history presented by clinical trial group staff as recorded on the CRFs. The team then scrolled through the images, with one investigator leading the image evaluation on the workstation. As each case was reviewed, the suspicious findings were compared to those reported by the unblinded and blinded readers. In all cases, the blinded reader was in agreement with the unblinded reader at the conclusion of the review. Indeed, all investigators were in agreement on all findings on all patients with one exception (an indeterminate recurrence in the prostate bed versus physiologic uptake in smooth muscle).

At the conclusion of the discordant case review, the readers requested a group review of all remaining cases, using the same reading format. These reads further refined the read methodology and the consensus summarisation of findings. Table 2 provides a summary of this review.

TABLE 2

Review of Discordant Cases

| Area of Discordant Findings | Unblinded Confidence | Blinded Confidence |
|---|---|---|
| Prostate bed | 5 | 1 |
| L3 Superior endplate | 5 | 2 (Schmorl's node) |
| Unblinded investigator initially thought L3 Superior endplate was a Schmorl's node. Confirmed metastasis with standard of care imaging and clinical follow-up. | | |
| Prostate base | 2 | Left 5, Right 4 4 (independent) |
| Unblinded investigator called 'probably negative;' however, blinded and independent reader read as probably and definitely positive. The unblinded investigator changed the assessment to probably positive (left 4, right 3) after the group review. Lymph nodes findings (4 nodes) were concordant across all readers. | | |
| Internal iliac right lymph node | 4 | 3 |
| The node was confirmed positive with standard of care imaging and clinical follow-up. The blinded reader changed the confidence to 4 following group review. The bone lesion in the skull had been reviewed previously be the blinded reader so was not discussed. | | |
| Retrocaval lymph node | 4 | 1. Not noted 2. Not noted |
| Liver | 2-3 | 1. Benign cyst 2. 4 |
| After group review, both blinded readers called the retrocaval lymph node positive. A common iliac node was concordant. Ultrasound of the liver showed simple cysts. Blinded reader 1 correctly identified the lesion as a benign cyst. Blinded reader2 changed the assessment to benign cyst. | | |
| Right high obturator node | 3 | 5 |
| Following the group review, both the unblinded and blinded readers changed the confidence to 4. Positive findings in the prostate bed were concordant. Of note, the patient received a dose of 250 MBq (wt. = 94 kg), producing a sub-optimal image. | | |
| Prostate bed | Not noted | 4 |
| Unblinded investigator assessed the prostate bed as 'probably negative.' The two blinded readers who were seeing the images for the first time gave a confidence of equivocal. There was no patient follow-up to confirm result. | | |
| L3 vertebrae | 2 | 5 |
| L5 vertebrae | 2 | 5 |
| Unblinded investigator read L3 as a Schmorl's node and L5 as degenerative changes. Blinded reader assigned a confidence interval of 5 to both vertebrae. Following the group review, the unblinded investigator increased to 3, the blinded reader decreased to 4, and investigators from the two other sites assessed a 3 and a 4, during the consensus discussion. Two lymph nodes were read as concordant. | | |
| Right 10$^{th}$ rib | 5 | 4 4 Not noted |
| Prostate bed* (not discordant) | 3-4 | 1 1 1 |
| This case had 3 blinded readers; one did not note the rib lesion. It should be noted that the unblinded investigator initially missed this lesion, but it was found on a retrospective review. The unblinded investigator initially called the prostate bed as equivocal to probable. This was a false positive as confirmed by biopsy. All blinded readers interpreted the images correctly. | | |

SUMMARY

Over the course of the meeting, the group collectively reviewed 32 FACBC PET/CT image data sets. Fourteen patients were primary prostate cancer patients and had not had a prostatectomy; 18 patients were status post-prostatectomy. There were 23 paired blinded and unblinded written image read assessments. These formed the basis for the determination of the 8 discordant findings and 15 concordant patients. It should be noted that cases with a discordant finding had other findings that were concordant. The ability of the investigators to correctly read the images with no clinical history was well-documented.

Discordant cases were an important part of the learning experience for the discussants, since it resulted in changes in their interpretation criteria. Two sites shifted their sensitivity for reporting focal abnormal uptake, bringing them in line with the remainder of the group.

A summary of the standardized patient preparation and image acquisition and reconstruction parameters are presented in Table 3.

TABLE 3

Image Acquisition, Reconstruction, and Interpretation Guidelines

| | |
|---|---|
| Scanner(s) | Use highest quality scanner available |
| Patient preparation | Fast >4 hrs, nothing by mouth except sips of water for medications No significant exercise from day before scan through to scan |
| Acquisition mode | 3D (if available) |
| CT | High-quality CT, no contrast in clinical study, 3 mm slice thickness maximum |
| Administered dose | 370 MBq +/− 20% (dosage below that range result in low-quality images). Administer dose with arms down, into right arm if possible. Dilute dosage up to 10 ml, slow push over 1 minute, ≧10 ml flush. Move arms back to scanning position following dose and flush. |
| Position: | Supine |
| Arm Position | Behind head |
| Start Scan | Proximal thigh |
| End Scan | Base of skull |
| Minutes per bed pos. | 3 min per bed position with up to 5 minutes for first two bed positions (single static scan) |
| Number of bed pos. | 4-5 as needed (depends on scanner field of view) |
| Uptake time initial | 3-5 minutes with a goal of 4 minutes from the end of injection |
| Reconstruction | Use Point-Response-Function reconstruction (resolution recovery or modulating) if available for visual assessment. For quantitative assessment, images should be reconstructed with 2 to 3 iterations, 20 to 28 subsets, and Gaussian post reconstruction filter with 3-6 mm (dependent on scanner) |

It is believed that utilization of these standardized interpretation criteria may help to improve disease management, streamline patient care and reduce unnecessary treatments and medical costs.

Read Consensus for Recurrent Prostate Cancer

Following the consensus group read of the 32 image sets, the group summarized the read interpretation criteria for recurrent prostate cancer. The criteria use a comparison to background tissue to assign a relative uptake level. Uptake is defined as mild if the SUV of the area of interest is greater than the SUV of the blood pool in the descending aorta. Moderate uptake is defined as an SUV greater than bone marrow, typically in the lumbar vertebrae 3. Intense uptake is defined as an SUV value greater than that of the liver.

Prostate:

In general, as with other PET radiotracers, the more intense and nonphysiologic the uptake, the greater the possibility of a true positive.

In the prostate bed in a patient who has had a prostatectomy, non-physiological uptake which is visually equal to marrow is suspicious for disease. But if a focus is small (<1 cm) and thus subject to partial volume effect and in a suspicious location, it may still call suspicious if it is visually greater than blood pool.

In the prostate bed in a patient who has not had a prostatectomy, moderate focal, asymmetric uptake visually greater than marrow is suspicious for residual or recurrent cancer. But if a focus is small (<1 cm or <0.7 cm when a resolution recovery reconstruction algorithm is used) it may still be called suspicious because the uptake will be underestimated, due to partial volume effect, if visually greater than blood pool. Underestimation is valid not only for quantification, but for visual assessment, as well. If the uptake is diffuse, heterogeneous and significantly greater than blood pool, it would be considered suspicious for disease (visually apparent). If the uptake is diffuse and homogenous, a threshold of significantly greater than marrow (visually apparent) would apply. Anecdotally, median lobe uptake (central base invaginating into bladder) has a higher Fluciclovine uptake than peripheral and central zones.

Extra-Prostate:

Ratios indicative of malignancy for suspected disease in the lymph nodes are dependent upon the size and the location of the nodes. If the suspicious site is in a lymph node chain that is typical for prostatic metastases, an uptake visually greater than marrow at L3 is considered suspicious. [ROC analysis of nodes of all sizes maximizes sensitivity and specificity with a node (SUVmax) to marrow (SUVmean at L3) ratio of 1.2 or greater]. But if a node is small (<1 cm or <0.7 cm when a resolution recovery reconstruction algorithm is used) and subject to partial volume effect and in a suspicious location, it may still be called suspicious if it is visually equal to marrow or significantly greater than blood pool (recommend 1.5-2×).

For inguinal, distal external iliac, and axillary nodes, mild, symmetric slightly increased uptake is considered physiologic uptake. But if the node is present within the context of other clear disease, it may also be considered suspicious. The presence of nearby vascular grafts or orthopaedic hardware could cause false positive uptake in these nodal groups. In addition, distal external iliac nodes may also be suspicious in isolation if above causes of false positivity are excluded including recent procedures and if the activity is greater than marrow.

For disease sites in bone, there may occasionally be an inverse relationship between fluciclovine uptake and the disease seen on CT. Focal bone lesion seen on MIP or PET only, is suspicious for disease. Sclerotic lesions showing cortical bone structure typical for benign osteomas on CT, without fluciclovine uptake are regarded as benign. In patients receiving antiandrogene therapy or after focal radiation therapy of local bone metastases a bone lesion seen on CT seen as dense sclerosis, with no focal uptake of fluciclovine on PET, is regarded as equivocal.

Sclerotic lesions with slightly, moderate or dense sclerosis or osteolysis on CT and focal elevated fluciclovine uptake are suspicious for disease. Bone metastases which resemble Schmorl's nodes, but with fluciclovine uptake within them, have been described. Correlation with CT scan, especially diagnostic, can be helpful in these cases.

Distribution of yellow and red bone marrow and can lead to focal areas with slightly increased fluciclovine uptake in normal bone and make the appearance heterogeneous. If bone metastases are suspected, but fluciclovine results are negative, further evaluation with skeletal examinations such as MRI, NaF PET/CT or bone scan with SPECT/CT may be needed as fluciclovine alone may not be able to exclude metastases with 100% confidence.

Although the present disclosure has been described above with reference to specific embodiments, it is not intended to be limited to the specific form set forth herein. Rather, the invention is limited only by the accompanying claims and, other embodiments than the specifics described above are equally possible within the scope of these appended claims.

The invention claimed is:

1. A method of using anti-1-amino-3-$^{18}$F-fluorocyclobutane-1-carboxylic acid ([$^{18}$F]-FACBC), comprising:
   a) administering the [$^{18}$F]-FACBC in a dose of 370 MBq as an intravenous bolus injection into a human subject having a suspected prostate cancer recurrence, wherein the [$^{18}$F]-FACBC injection is followed by an intravenous flush; and
   b) acquiring a positron emission tomography (PET) scan image of the human subject during a PET scan;
   wherein the human subject has:
      i. consumed no food or drink including water for at least 4 hours prior to the injection, except sips of water for taking medications, and
      ii. avoided significant exercise for at least one day prior to the PET scan;
   wherein the human subject is positioned in a supine position with arms above the head before the PET scan starts;
   wherein the PET scan starts 3 to 5 minutes after the end of the [$^{18}$F]-FACBC injection;
   and
   wherein the PET scan starts from at least the human subject's proximal thigh and proceeds to the base of the human subject's skull for a total scan time of up to 30 minutes.

2. The method of claim 1, further comprising analysing the PET scan image for a small lesion less than 1 cm at a suspicious location, and identifying the lesion as suspicious for the prostate cancer recurrence if an uptake of [$^{18}$F]-FACBC by the lesion is greater than blood pool.

* * * * *